US012778815B2

(12) United States Patent
Lee et al.

(10) Patent No.: US 12,778,815 B2
(45) Date of Patent: Nov. 3, 2026

(54) NASAL CAVITY PACKING STRUCTURE

(71) Applicants: Si Woo Lee, Seoul (KR); Tae Ho Ha, Seoul (KR)

(72) Inventors: Si Woo Lee, Seoul (KR); Tae Ho Ha, Seoul (KR)

(73) Assignees: Si Woo Lee, Seoul (KR); Tae Ho Ha, Seoul (KR)

( * ) Notice: Subject to any disclaimer, the term of this patent is extended or adjusted under 35 U.S.C. 154(b) by 459 days.

(21) Appl. No.: 18/015,429

(22) PCT Filed: Jul. 14, 2021

(86) PCT No.: PCT/KR2021/009026
§ 371 (c)(1),
(2) Date: Jan. 10, 2023

(87) PCT Pub. No.: WO2022/015042
PCT Pub. Date: Jan. 20, 2022

(65) Prior Publication Data

US 2023/0285203 A1 Sep. 14, 2023

(30) Foreign Application Priority Data

Jul. 15, 2020 (KR) ........................ 10-2020-0087610

(51) Int. Cl.
*A61F 13/20* (2006.01)
*A61F 13/36* (2006.01)
*A61L 15/22* (2006.01)

(52) U.S. Cl.
CPC ...... *A61F 13/2005* (2013.01); *A61F 13/2042* (2013.01); *A61F 13/2051* (2013.01);
(Continued)

(58) Field of Classification Search
CPC ...... A61F 13/36; A61F 13/20; A61F 13/2005; A61F 11/10; A61F 13/2042;
(Continued)

(56) References Cited

U.S. PATENT DOCUMENTS 4,030,504 A * 6/1977 Doyle ................. A61F 13/2028 606/199
5,336,163 A * 8/1994 DeMane ................. A61F 13/36 604/11
(Continued)

FOREIGN PATENT DOCUMENTS

EP 3228264 A1 10/2017
JP 2012515608 A 7/2012
(Continued)

OTHER PUBLICATIONS

Jeong, Da-won, International Search Report, PCT/KR2021/009026, Dated: Oct. 25, 2021; 2 pages.

*Primary Examiner* — Jacqueline F Stephens
*Assistant Examiner* — Meagan Ngo
(74) *Attorney, Agent, or Firm* — Kevin R. Erdman; Brannon Sowers & Cracraft PC

(57) ABSTRACT

The present invention provides a nasal cavity packing structure which comprises: a pad extending along a first direction, having a shape pressed in a second direction perpendicular to the first direction, and including a first hollow extending along the first direction inside the pad; and an elastic tube an outer circumferential surface of which is closely adhered to an inner circumferential surface of the pad.

9 Claims, 7 Drawing Sheets

(52) U.S. Cl.
CPC .......... *A61F 13/2071* (2013.01); *A61F 13/36* (2013.01); *A61L 15/22* (2013.01)

(58) Field of Classification Search
CPC .......... A61F 13/126; A61F 2013/00476; A61F 13/2017; A61F 13/12; A61F 13/2051; A61F 13/2071
See application file for complete search history.

(56) References Cited

U.S. PATENT DOCUMENTS

| | | | | |
|---|---|---|---|---|
| 5,584,827 | A * | 12/1996 | Korteweg | A61F 13/126 604/11 |
| 5,601,594 | A * | 2/1997 | Best | A61F 5/08 606/199 |
| 6,191,341 | B1 * | 2/2001 | Shippert | A61F 13/36 604/385.18 |
| 6,666,211 | B1 * | 12/2003 | Awoniyi | A61F 13/2005 128/858 |
| 10,736,792 | B1 * | 8/2020 | Fischell | A61F 13/55175 |
| 2005/0056289 | A1 * | 3/2005 | Jenkins | A61F 11/10 128/857 |
| 2007/0100370 | A1 | 5/2007 | Hogle | |
| 2009/0005763 | A1 * | 1/2009 | Makower | A61B 5/411 424/9.1 |
| 2009/0306575 | A1 * | 12/2009 | East | A61F 13/2074 604/11 |
| 2010/0130907 | A1 * | 5/2010 | Linkel | A61F 13/206 156/196 |
| 2012/0046607 | A1 * | 2/2012 | Syk | A61F 13/36 604/103.02 |
| 2013/0116656 | A1 * | 5/2013 | Song | A61F 13/126 604/285 |
| 2015/0209191 | A1 * | 7/2015 | Bruce | A61F 5/34 604/2 |
| 2018/0289383 | A1 * | 10/2018 | Fischell | A61B 17/24 |
| 2019/0029880 | A1 * | 1/2019 | DuBois | A61F 7/03 |

FOREIGN PATENT DOCUMENTS

| | | | |
|---|---|---|---|
| KR | 10-2017-0118198 | A | 10/2017 |
| KR | 10-2018-0082430 | A | 7/2018 |

* cited by examiner

【Figure 1】
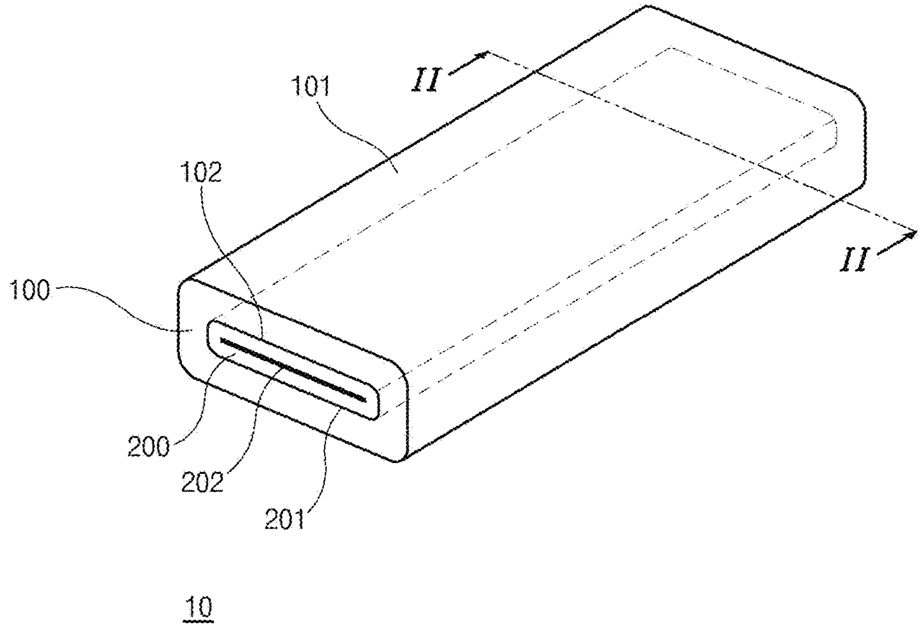
【Figure 2】
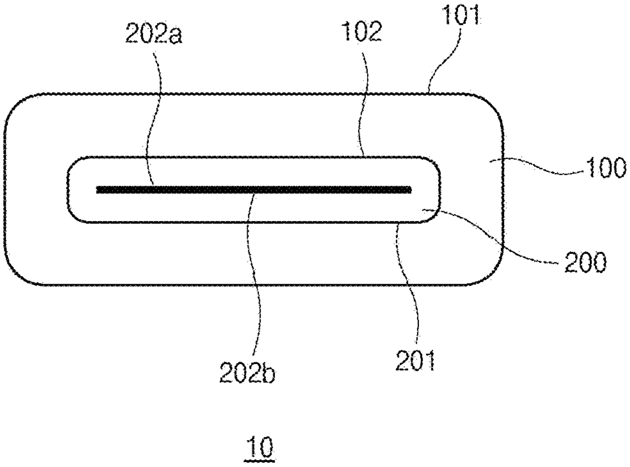

【Figure 3】
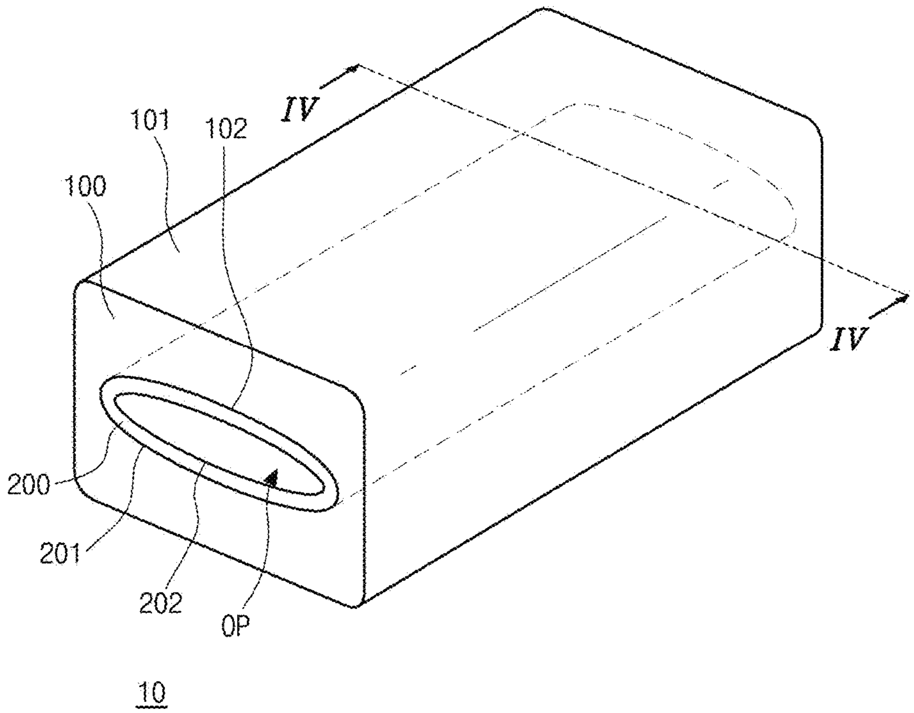
【Figure 4】
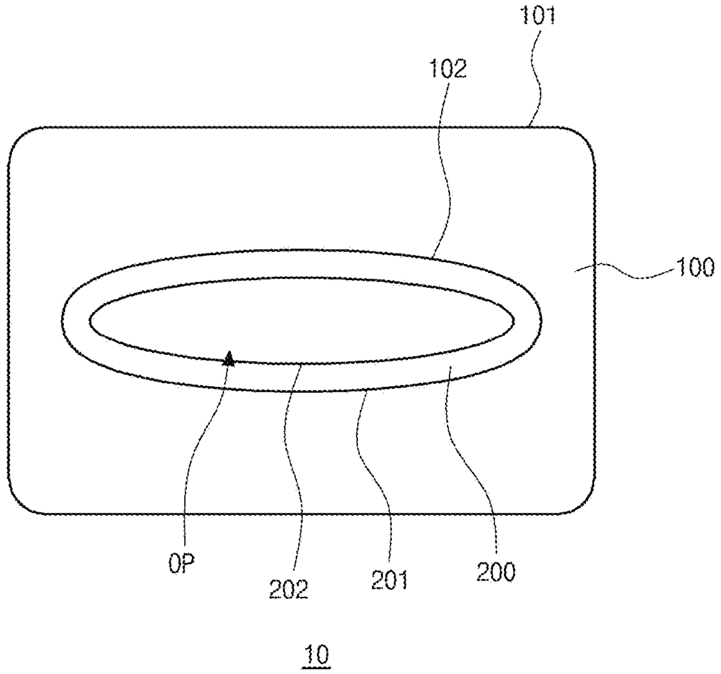

【Figure 5】
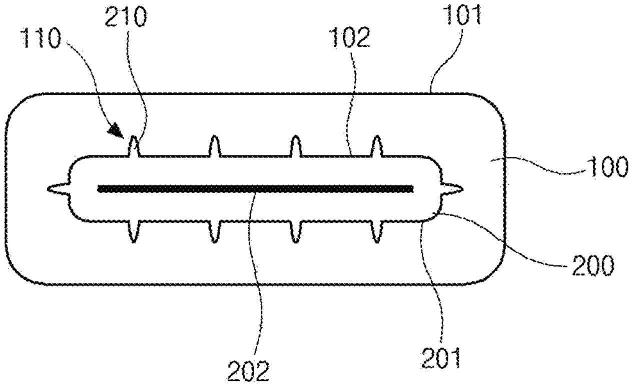
10
【Figure 6】
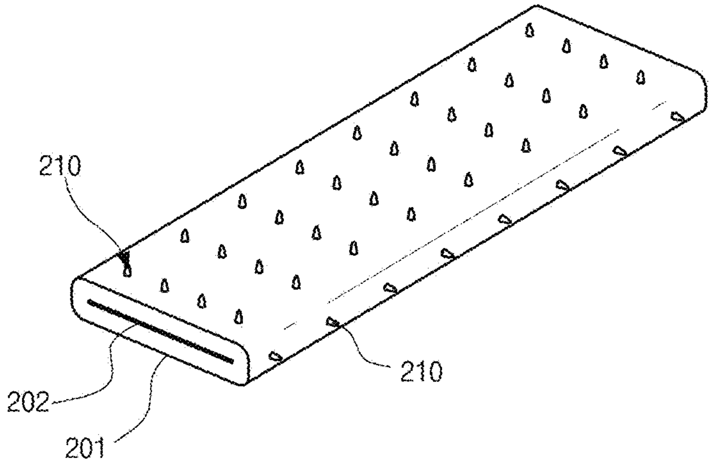
200

【Figure 7】
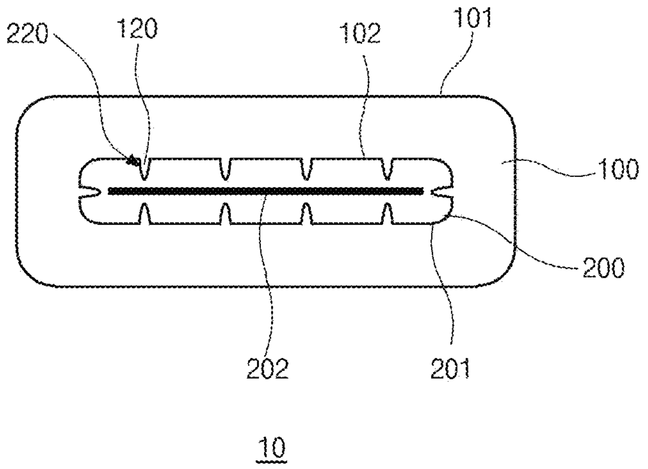
【Figure 8】
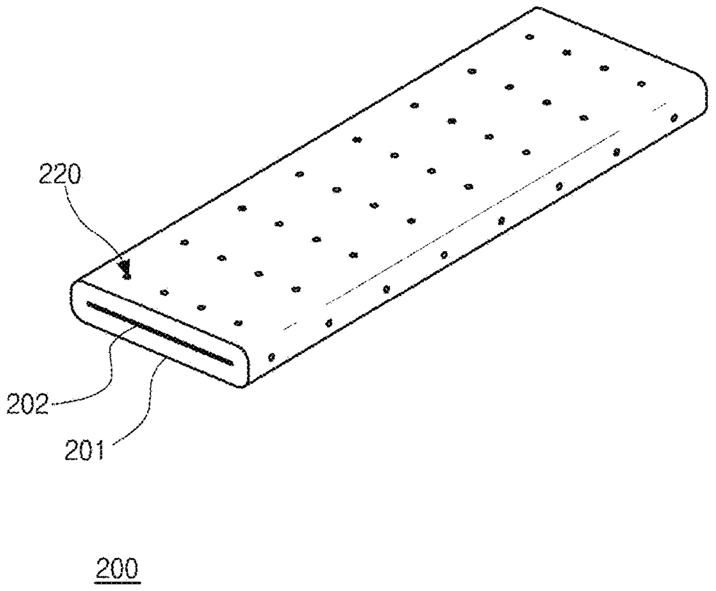

【Figure 9】
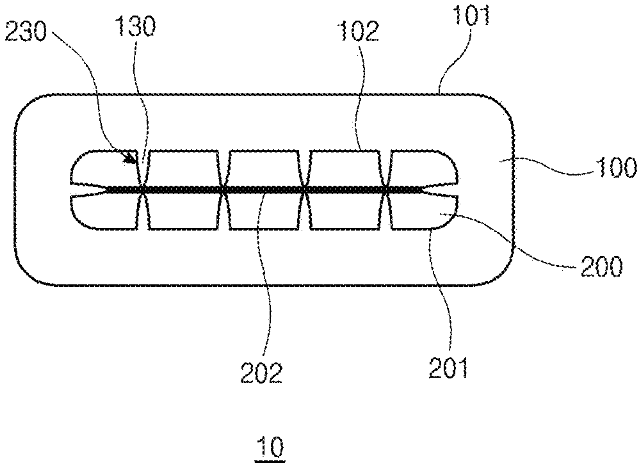
【Figure 10】
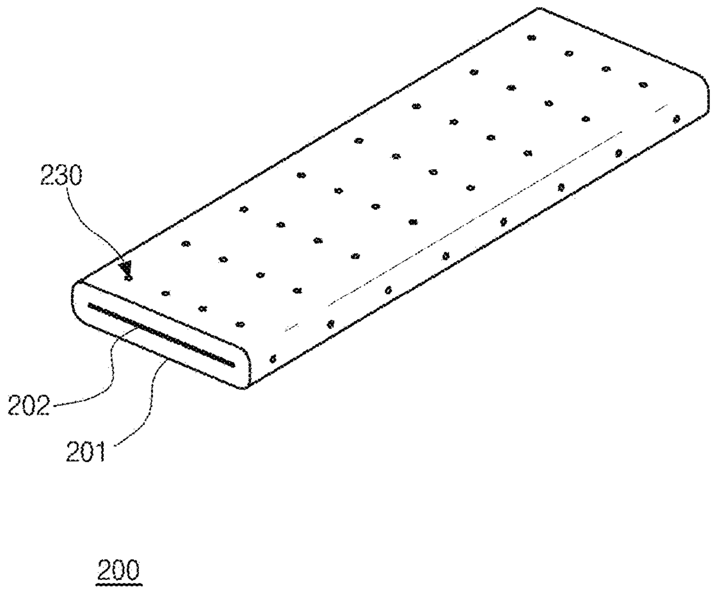

【Figure 11】
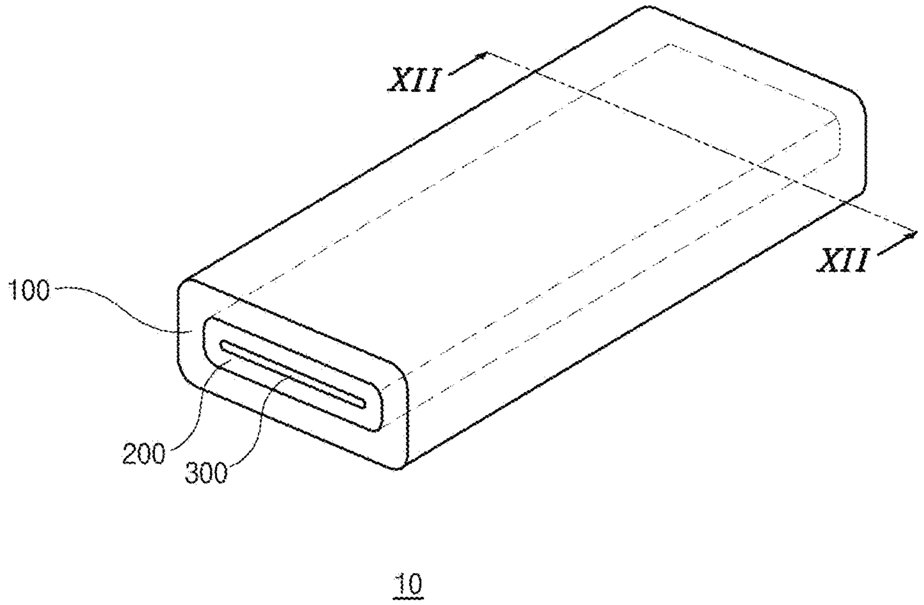
【Figure 12】
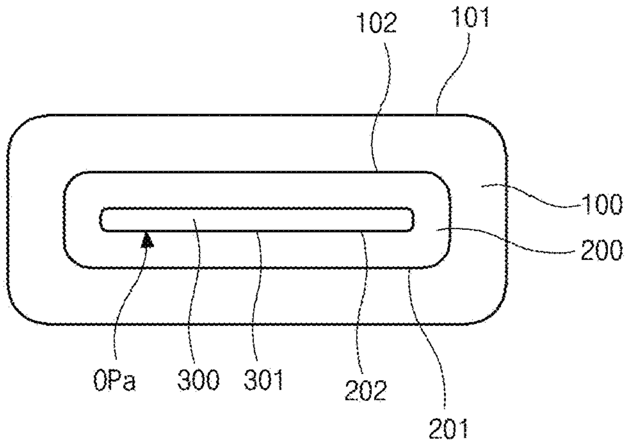

【Figure 13】
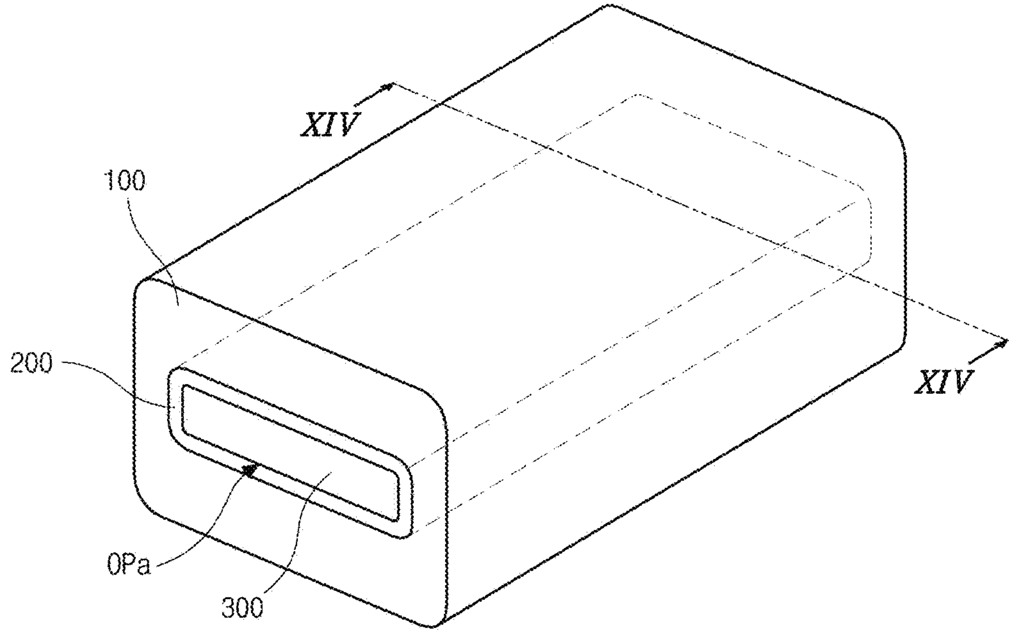
【Figure 14】
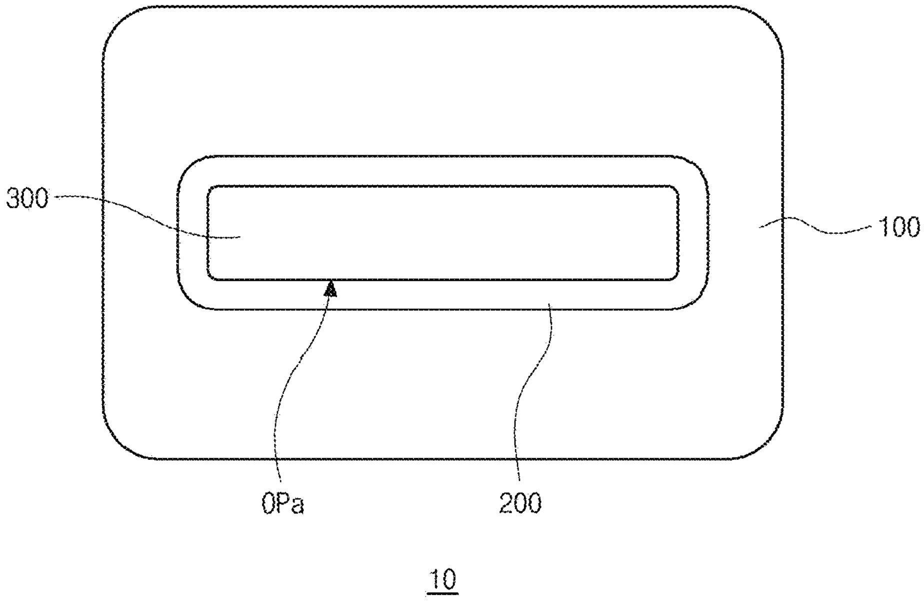

NASAL CAVITY PACKING STRUCTURE

TECHNICAL FIELD

The present invention relates to a nasal cavity packing structure that is a structure inserted into a nasal cavity.

BACKGROUND ART

In nose surgery or intranasal surgery performed in plastic surgery or otolaryngology, a packing structure may be inserted into a nasal cavity to maintain a shape of a nose, to conduct hemostasis in the nasal cavity, or the like.

In general, the packing structure has an approximately bar shape, and expands in volume by absorbing liquid. The expanded packing structure is closely adhered to and pressurizes a skin or mucous membrane in the nasal cavity.

However, since the packing structure inserted into the nasal cavity substantially blocks the entire nasal cavity, a user cannot breathe through the nose and thus considerable discomfort is caused.

DETAILED DESCRIPTION OF INVENTION

Technical Problem

An object of the present invention is to provide a nasal cavity packing structure which can allow breathing through a nasal cavity and thus alleviate discomfort.

Technical Solution

In order to achieve the above-mentioned object, the present invention provides a nasal cavity packing structure which includes: a pad extending along a first direction, having a shape pressed in a second direction perpendicular to the first direction, and including a first hollow extending along the first direction inside the pad; and an elastic tube an outer circumferential surface of which is closely adhered to an inner circumferential surface of the pad.

The elastic tube may have a state in which first and second portions of an inner circumferential surface facing each other are closely adhered to and contact each other.

A coating film may be formed on an inner circumferential surface of the elastic tube, and a viscosity of the coating film may be smaller than a viscosity of the elastic tube.

The elastic tube may include a plurality of protrusions protruding outward from its outer circumferential surface, and the pad may include a groove or a through hole into which the protrusion is inserted.

The elastic tube includes a plurality of concave grooves recessed inward from its outer circumferential surface or a plurality of through holes penetrating therethrough, and the pad may include a protrusion inserted into the concave groove or through hole.

An auxiliary pad filling a second hollow inside the elastic tube may be further included.

The auxiliary pad may include a material identical to or different from that of the pad.

The pad may have characteristic of absorbing liquid to expand in volume.

The pad and the auxiliary pad may have characteristic of absorbing liquid to expand in volume, and an expansion rate of the auxiliary pad may be equal to or different from an expansion rate of the pad.

The pad may include polyvinyl alcohol, polyvinyl acetate, or polyurethane.

Advantageous Effects

In the present invention, by disposing the elastic tube at the inner side of the pad of the nasal cavity packing structure, the hollow can be provided in the expanded state. Accordingly, smooth breathing through the hollow can be realized, so that a user's discomfort can be alleviated.

In addition, the restoring force of the elastic tube can be applied to the expanded pad, so that the close adhesion of the pad to the skin or mucous membrane can be improved, and thus the supporting force or hemostatic ability can be improved.

DESCRIPTION OF DRAWINGS

FIG. 1 is a perspective view schematically illustrating a nasal cavity packing structure in a pressed state according to a first embodiment of the present invention.

FIG. 2 is a cross-sectional view taken along a cut line II-II of FIG. 1.

FIG. 3 is a perspective view illustrating an example of a state in which a nasal cavity packing structure of FIG. 1 is expanded.

FIG. 4 is a cross-sectional view taken along a cut line IV-IV of FIG. 3.

FIG. 5 is a cross-sectional view schematically illustrating a first example of a nasal cavity packing structure in a pressed state according to a second embodiment of the present invention.

FIG. 6 is a perspective view schematically illustrating an elastic tube of a nasal cavity packing structure of FIG. 5.

FIG. 7 is a cross-sectional view schematically illustrating a second example of a nasal cavity packing structure in a pressed state according to a second embodiment of the present invention.

FIG. 8 is a perspective view schematically illustrating an elastic tube of a nasal cavity packing structure of FIG. 7.

FIG. 9 is a cross-sectional view schematically illustrating a third example of a nasal cavity packing structure in a pressed state according to a second embodiment of the present invention.

FIG. 10 is a perspective view schematically illustrating an elastic tube of a nasal cavity packing structure of FIG. 9.

FIG. 11 is a perspective view schematically illustrating a nasal cavity packing structure in a pressed state according to a third embodiment of the present invention.

FIG. 12 is a cross-sectional view taken along a cut line XII-XII of FIG. 11.

FIG. 13 is a perspective view illustrating an example of a state in which a nasal cavity packing structure of FIG. 11 is expanded.

FIG. 14 is a cross-sectional view taken along a cut line XIV-XIV of FIG. 13.

MODE FOR INVENTION

Hereinafter, embodiments of the present invention are described in detail with reference to the drawings.

First Embodiment

FIG. 1 is a perspective view schematically illustrating a nasal cavity packing structure in a pressed state according to a first embodiment of the present invention, and FIG. 2 is a cross-sectional view taken along a cut line II-II of FIG. 1. FIG. 3 is a perspective view illustrating an example of a state in which a nasal cavity packing structure of FIG. 1 is expanded, and FIG. 4 is a cross-sectional view taken along a cut line IV-IV of FIG. 3.

Referring to FIGS. 1 to 4, the nasal cavity packing structure 10 (or nasal cavity packer) of this embodiment may be formed to, for example, have an approximate bar shape extending along a first direction, for example, along a longitudinal direction.

Such the nasal cavity packing structure 10 may be formed to have a pressed (or compressed) state in appearance as an initial product state. In this regard, referring to FIGS. 1 and 2, the nasal cavity packing structure 10 may be formed to have a pressed state in a second direction substantially perpendicular to a first direction, for example, in a thickness direction. That is, the nasal cavity packing structure 10 may be formed in a pressed form (or shape) in the thickness direction toward the inside thereof. In other words, the nasal cavity packing structure 10 may have a thickness in the second direction which is smaller than a width in a third direction perpendicular to both the first and second directions, and may have a shape pressed in the second direction in appearance.

Meanwhile, when the pressed nasal cavity packing structure 10 is provided with liquid such as water or bodily fluid, the pressed nasal cavity packing structure 10 may absorb the liquid and expand toward the outside. In this regard, referring to FIGS. 3 and 4, the nasal cavity packing structure 10 may be configured so that its volume expands in the thickness direction toward the outside as a direction substantially opposite to the press direction.

As such, an outer circumferential surface of the expanded nasal cavity packing structure 10 may be closely adhered to a skin or mucous membrane of the nasal cavity and the expanded nasal cavity packing structure 10 may pressurize the skin or mucous membrane. Accordingly, it is possible to maintain a shape of the nose or to achieve hemostasis in the nasal cavity.

The expansion process of the nasal cavity packing structure 10 as described above may be performed before and/or in a state of being inserted into the nasal cavity.

As above, the "pressed" state of the nasal cavity packing structure 10 in this embodiment may mean the state of the nasal cavity packing structure 10 prior to becoming an "expanded" state by absorbing liquid. As such, the nasal cavity packing structure 10 may have characteristic of a sponge.

The nasal cavity packing structure 10 in the expanded state inserted into the nasal cavity may have a hollow OP extending therein along the longitudinal direction. As such, since the hollow OP is provided inside, a user can smoothly breathe through the nasal cavity through the hollow OP, so that discomfort can be significantly alleviated.

As such, the nasal cavity packing structure 10 which provides the hollow OP as a breathing passage in the expanded state may includes a pad 100, which is a component disposed at an outer side of the nasal cavity packing structure 10, and an elastic tube 200 disposed at an inner side of the pad 100.

The pad 100 may have a porous structure and may be configured to have characteristic of expanding in volume by absorbing liquid such as water or bodily fluid in a pressed state (or compressed state). In this regard, the pad 100 may be formed using a material of expansion characteristic, for example, polyvinyl alcohol, polyvinyl acetate, polyurethane, or the like, but is limited thereto.

Such the pad 100 may be a component located at the outer side of the nasal cavity packing structure 10 and may define appearance of the nasal cavity packing structure 10.

When the nasal cavity packing structure 10 is inserted into the nasal cavity, the outer circumferential surface 101 of the pad 100 in the expanded state may be in direct contact with and press the skin or mucous membrane in the nasal cavity.

The elastic tube 200 is a component located at an inner side of the pad 100, and an outer circumferential surface 201 of the elastic tube 200 may be configured to be closely adhered to and contact an inner circumferential surface 102 of the pad 100.

The elastic tube 200 may be formed of a material having elasticity. In this regard, the elastic tube 200 may use a rubber, for example, may be formed using a biocompatible compound of silicone, polyurethane, polyethylene, polypropylene, polypropylene, teflon, prolene, nylon, polydioxanone, polyglycolic acid, polylactic acid, polyglyco-lactic acid, or the like, but is not limited thereto.

In the pressed state of the nasal cavity packing structure 10 as shown in FIGS. 1 and 2, the pad 100 is in the pressed state. In addition, as an external force (or pressing force) by the pad 100 in the pressed state acts on the elastic tube 200, the elastic tube 200 becomes pressed in an inward direction and is fixed in shape in this state and has a restoring force toward the outside. In such the pressed state, the volume of the nasal cavity packing structure 10 may be substantially minimized.

As such, in the pressed state of the nasal cavity packing structure 10, the pad 100 may provide a hollow in the pressed state, and the elastic tube 200 in the compressed state may fill the hollow.

In addition, in such the pressed state, the inner circumferential surface 202 of the elastic tube 200 may have a state closely adhered in the press direction. In this regard, referring to FIGS. 1 and 2, for example, a first portion 202*a* and a second portion 202*b*, which are portions of the inner circumferential surface 202 facing each other in the press direction, may have a state in which they are closely adhered to and contact each other. In this state, the elastic tube 200 does not substantially provide a hollow.

Meanwhile, when the pad 100 is expanded by being provided with liquid as shown in FIGS. 1 and 2, the pressing force of the pad 100 to the elastic tube 200 is reduced, and the elastic tube 200 is deformed in shape so that the inner circumferential surface 202 moves in an outward direction by the restoring force. Accordingly, the hollow OP can be finally provided inside the elastic tube 200.

As such, by using the elastic tube 200, the expanded nasal cavity packing structure 10 can have the hollow OP, so that smooth breathing can be realized through the hollow OP.

In addition, the restoring force of the elastic tube 200 can be applied to the expanded pad 100, thus close adhesion of the pad 100 to the skin or mucous membrane can be improved, and thus a supporting force or hemostasis ability can be improved.

Meanwhile, a coating film may be formed on the inner circumferential surface 202 of the elastic tube 200. In this regard, when the pressed state lasts for a long time, as the closely adhered state of the inner circumferential surface 202 of the elastic tube 200 is maintained for a long time, the closely adhered portions of the inner circumferential surface may get stuck, so that even if the pad 100 expands, the closely adhered state of the elastic tube 200 may not be released. Accordingly, by forming the coating film on the inner circumferential surface 202, an adhesive force between the portions of the inner circumferential surface which are closely adhered to each other is reduced, so that the closely adhered state can be released smoothly.

Such the coating film may be formed of a material having a viscosity lower than that of the elastic tube 200, so that an inner surface of the coating film may have smoother characteristic (or lower roughness characteristic) than the elastic tube 200. In this regard, the surface of the coating film may be configured to have a lower frictional force than the surface of the elastic tube 200.

Meanwhile, when the coating film is formed, the coating film may be formed on at least a portion of the inner circumferential surface 202 of the elastic tube 200. Regarding the case where the coating film is formed on a portion, parts of the coating film on the inner circumferential surface 202 of the elastic tube 200 may be configured to be spaced apart from each other and distributedly disposed.

Second Embodiment

In the second embodiment, detailed descriptions of components identical and similar to those of the first embodiment may be omitted.

FIG. 5 is a cross-sectional view schematically illustrating a first example of a nasal cavity packing structure in a pressed state according to a second embodiment of the present invention, and FIG. 6 is a perspective view schematically illustrating an elastic tube of a nasal cavity packing structure of FIG. 5.

Referring to FIGS. 5 and 6, in the nasal cavity packing structure 10 of the first example of this embodiment, the elastic tube 200 may be configured to have a plurality of protrusions 210 protruding outward from its outer circumferential surface 201. Such the protrusions 210 may be uniformly or randomly disposed at at least a region of the outer circumferential surface 201.

The protrusion 210 may have various shapes including a polyhedron or a cylinder. In addition, the protrusion 210 may have various shapes, including a shape extending in one direction when viewed in plan.

In addition, when viewed in cross-section, the protrusion 210 may have a shape in which a width (or thickness) is substantially the same, becomes smaller, or becomes larger toward an outer direction.

As such, as the protrusion 210 is provided, the outer circumferential surface 201 of the elastic tube 200 may have a concave-convex shape.

As the inner circumferential surface 102 of the pad 100 is closely adhered to and contact the outer circumferential surface 201 of the elastic tube 200 at which the protrusions 210 are formed, the inner circumferential surface 102 may have grooves 110 (or through holes) corresponding to the protrusions 210. In this embodiment, a structure in which the groove 110, into which the protrusion 210 is inserted, is formed corresponding to the protrusion 210 is taken as an example.

As described above, by forming the protrusion 210, an area of a closely adhered surface between the elastic tube 200 and the pad 100 can increase, so that an adhesive force between the elastic tube 200 and the pad 100 can be improved. In addition, the outer circumferential surface 201 of the elastic tube 200 has a concavo-convex shape due to the protrusions 210, so that the elastic tube 200 relatively moving and slipping along the longitudinal direction with respect to the pad 100 can be prevented (or reduced). In addition, the outer circumferential surface 201 of the elastic tube 200 has a concavo-convex shape due to the protrusions 210, so that the elastic tube 200 relatively moving and slipping along a circumferential direction with respect to the pad 100 can be prevented (or reduced).

FIG. 7 is a cross-sectional view schematically illustrating a second example of a nasal cavity packing structure in a pressed state according to a second embodiment of the present invention, and FIG. 8 is a perspective view schematically illustrating an elastic tube of a nasal cavity packing structure of FIG. 7.

Referring to FIGS. 7 and 8, in the nasal cavity packing structure 10 of the second example of this embodiment, the elastic tube 200 may be configured to have a plurality of concave grooves 220 recessed from its outer circumferential surface 201 to the inside. Such the concave grooves 220 may be uniformly or randomly disposed at at least a region of the outer circumferential surface 201.

The concave groove 220 may have various shapes including a polyhedron or a cylinder. In addition, the concave groove 220 may have various shapes, including a shape extending in one direction when viewed in plan.

In addition, when viewed in cross-section, the concave groove 220 may have a shape in which a width (or thickness) is substantially the same, becomes smaller, or becomes larger toward an outer direction.

As such, as the concave groove 220 is provided, the outer circumferential surface 201 of the elastic tube 200 may have a concave-convex shape.

As the inner circumferential surface 102 of the pad 100 is closely adhered to and contact the outer circumferential surface 201 of the elastic tube 200 at which the concave grooves 220 are formed, the inner circumferential surface 102 may have protrusions 120 corresponding to and inserted into the concave grooves 220.

As described above, by forming the concave groove 220, an area of a closely adhered surface between the elastic tube 200 and the pad 100 can increase, so that an adhesive force between the elastic tube 200 and the pad 100 can be improved. In addition, the outer circumferential surface 201 of the elastic tube 200 has a concave-convex shape due to the concave grooves 220, so that the elastic tube 200 relatively moving and slipping along the longitudinal direction with respect to the pad 100 can be prevented (or reduced). In addition, the outer circumferential surface 201 of the elastic tube 200 has a concavo-convex shape due to the concave grooves 220, so that the elastic tube 200 relatively moving and slipping along a circumferential direction with respect to the pad 100 can be prevented (or reduced).

FIG. 9 is a cross-sectional view schematically illustrating a third example of a nasal cavity packing structure in a pressed state according to a second embodiment of the present invention, and FIG. 10 is a perspective view schematically illustrating an elastic tube of a nasal cavity packing structure of FIG. 9.

Referring to FIGS. 9 and 10, in the nasal cavity packing structure 10 of the third example of this embodiment, the elastic tube 200 may be configured to have a plurality of through holes 230 penetrating the elastic tube 200. Such the through holes 230 may be uniformly or randomly disposed at at least a region of the elastic tube 200.

The through hole 230 may have various shapes including a polyhedron or a cylinder. In addition, the through hole 230 may have various shapes, including a shape extending in one direction when viewed in plan.

In addition, when viewed in cross-section, the through hole 230 may have a shape in which a width (or thickness) is substantially the same, becomes smaller, or becomes larger toward an outer direction.

As such, as the through hole 230 is provided, the elastic tube 200 may have a concavo-convex shape, similar to the case where the concave groove 220 is formed.

As the inner circumferential surface 102 of the pad 100 is closely adhered to and contact the elastic tube 200 at which the through holes 230 are formed, the inner circumferential surface 102 may have protrusions 130 corresponding to and inserted into the through holes 230. Here, the protrusion 130 may have a height which is equal to, smaller than, or larger than a depth of the through hole 230.

As described above, by forming the through hole 230, an area of a closely adhered surface between the elastic tube 200 and the pad 100 can increase, so that an adhesive force between the elastic tube 200 and the pad 100 can be improved. In addition, the elastic tube 200 has a concavo-convex shape due to the through holes 230, so that the elastic tube 200 relatively moving and slipping along the longitudinal direction with respect to the pad 100 can be prevented (or reduced). In addition, the outer circumferential surface 201 of the elastic tube 200 has a concavo-convex shape due to the through holes 230, so that the elastic tube 200 relatively moving and slipping along a circumferential direction with respect to the pad 100 can be prevented (or reduced).

Meanwhile, regarding the expansion of the pad 100, liquid may flow into the pad 100 through the through hole 230. In addition, in the state in which the nasal cavity packing structure 10 is expanded, liquid contained in the pad 100 may be discharged to the hollow (OP of FIG. 3) of the elastic tube 200 through the through hole 230.

Meanwhile, when the protrusion 130 of the pad 100 substantially completely fills the through hole 230 and has a height equal to or greater than a height of the through hole 230, the protrusion 130 of the pad 100 (i.e., an end of the protrusion) may contact the inner circumferential surface 202 of the elastic tube 200. In this case, a phenomenon in which portions of the inner circumferential surface 202 of the elastic tube 200 get stuck to each other in the pressed state can be alleviated, so that release of the closely adhered state of the elastic tube 200 when the pad 100 expands can be made smoothly.

Meanwhile, this embodiment may include a combination of two structures or a combination of three structures among the protrusion structure of the first example, the concave groove structure of the second example, and the through hole structure of the third example.

Third Embodiment

In the third embodiment, detailed descriptions of components identical and similar to those of the first or second embodiment may be omitted.

FIG. 11 is a perspective view schematically illustrating a nasal cavity packing structure in a pressed state according to a third embodiment of the present invention, and FIG. 12 is a cross-sectional view taken along a cut line XII-XII of FIG. 11. FIG. 13 is a perspective view illustrating an example of a state in which a nasal cavity packing structure of FIG. 11 is expanded, and FIG. 14 is a cross-sectional view taken along a cut line XIV-XIV of FIG. 13.

Referring to FIGS. 11 and 12, the nasal cavity packing structure 10 in a pressed state of this embodiment may include an auxiliary pad 300 disposed on an inner side of the elastic tube 200 to be wrapped by the elastic tube 200. An outer circumferential surface 301 of the auxiliary pad 300 may be configured to be closely adhered to and contact the inner circumferential surface 202 of the elastic tube 200.

As such, in the pressed state of the nasal cavity packing structure 10, the elastic tube 200 may provide a hollow OPa in the pressed state, and the hollow OPa may be filled with the auxiliary pad 300.

As such, as the auxiliary pad 300 is provided inside the elastic tube 200, in the pressed state, the inner circumferential surface 202 of the elastic tube 200 does not have the closely adhered state in the press direction. In this regard, portions of the inner circumferential surface 202 facing each other in the press direction do not have a state of being closely adhered to and contacting each other, but have a state of being spaced apart from each other with the auxiliary pad 300 interposed.

Accordingly, a phenomenon in which the portions of the inner circumferential surface of the elastic tube 200 get stuck to each other in the pressed state can be prevented, so that release of the pressed state of the elastic tube 200 when the pad 100 expands can be made smoothly.

Such the auxiliary pad 300 may have the pressed state (or compressed state), similar to the pad 100, in the pressed state of the nasal cavity packing structure 10.

In this case, similar to the pad 100, the auxiliary pad 300 may have a porous structure and may have characteristic of absorbing liquid such as water or bodily fluid to expand in volume.

In this regard, referring to FIGS. 13 and 14, when liquid is provided, the pad 100 and the auxiliary pad 300 may expand. Accordingly, the elastic tube 200 interposed between the pad 100 and the auxiliary pad 300 may be deformed in shape to move outward. At this time, since an expansive force of the auxiliary pad 300 acts on the elastic tube 200 and the pad 100, a shape deformation of the elastic tube 200 in the outward direction can be further improved and a close adhesion of the pad 100 to the skin or mucous membrane can be further improved.

The expanded auxiliary pad 300 can be removed from the nasal cavity packing structure 10, and accordingly, the hollow OPa in the expanded state can be provided inside the elastic tube 200, through which smooth breathing can be realized.

Such the auxiliary pad 300 may be formed of the same material as the pad 100 and may have the same expansion rate as the pad 100, but is not limited thereto, and may be formed of a material different from the pad 100. When formed of a different expandable material, the auxiliary pad 300 may have a lower or higher expansion rate than the pad 100.

Meanwhile, the auxiliary pad 300 may be formed to have characteristic of maintaining its shape without substantially expanding by not substantially absorbing liquid. Even in this case, the auxiliary pad 300 can be removed from the expanded nasal cavity packing structure 10, and accordingly, the hollow OPa in the expanded state can be provided inside the elastic tube 200, through which smooth breathing can be realized.

Meanwhile, the present invention may include a combination of at least two of the first to third embodiments described above.

As described above, according to the present invention, by disposing the elastic tube at the inner side of the pad of the nasal cavity packing structure, the hollow can be provided in the expanded state. Accordingly, smooth breathing through the hollow can be realized, so that a user's discomfort can be alleviated.

In addition, the restoring force of the elastic tube can be applied to the expanded pad, so that the close adhesion of the pad to the skin or mucous membrane can be improved, and thus the supporting force or hemostatic ability can be improved.

The above-described embodiments of the present invention are examples of the present invention, and can be freely modified within the scope included in the spirit of the present invention. Accordingly, the present invention covers modifications of the present invention within the scope of the appended claims and their equivalents.

What is claimed is:

1. A nasal cavity packing structure comprising:

a pad extending along a first direction, having a shape pressed in a second direction perpendicular to the first direction, and including a first hollow extending along the first direction inside the pad, the pad having a pressed state and an expanded state; and an elastic tube, wherein an outer circumferential surface of the elastic tube is closely adhered to an inner circumferential surface of the pad, and an auxiliary pad filling a second hollow inside the elastic tube, wherein the pad and the auxiliary pad have the same length, and are comprised of material having an expansion characteristic.

2. The nasal cavity packing structure according to claim 1, wherein:

a coating film is formed on an inner circumferential surface of the elastic tube; and a viscosity of the coating film is smaller than a viscosity of the elastic tube.

3. The nasal cavity packing structure according to claim 1, wherein:

the elastic tube comprises a plurality of protrusions protruding outward from its outer circumferential surface, and the pad comprises a groove or a through hole into which the protrusion is inserted.

4. The nasal cavity packing structure according to claim 1, wherein:

the elastic tube comprises a plurality of concave grooves recessed inward from its outer circumferential surface or a plurality of through holes penetrating therethrough; and the pad comprises a protrusion inserted into the concave groove or through hole.

5. The nasal cavity packing structure according to claim 1, wherein the auxiliary pad comprises a material identical to or different from that of the pad.

6. The nasal cavity packing structure according to claim 1, wherein the pad has a characteristic of absorbing liquid to expand in volume.

7. The nasal cavity packing structure according to claim 1, wherein:

the pad and the auxiliary pad have a characteristic of absorbing liquid to expand in volume, and an expansion rate of the auxiliary pad is equal to or different from an expansion rate of the pad.

8. The nasal cavity packing structure according to claim 1, wherein the pad comprises polyvinyl alcohol, polyvinyl acetate, or polyurethane.

9. The nasal cavity packing structure according to claim 1, wherein the auxiliary pad has a first state when disposed in the second hollow and an expanded state, such that when the auxiliary pad is removed from the second hollow, to allow breathing through the second hollow of the elastic tube, the auxiliary pad extends to the expanded state.

* * * * *